(12) United States Patent
Lutze et al.

(10) Patent No.: US 6,652,744 B2
(45) Date of Patent: Nov. 25, 2003

(54) DEVICE FOR FILTERING AND REMOVING FLUIDS

(75) Inventors: Konstantin Lutze, Hombrechtikon (CH); Michael Collasius, Ratingen (CH); Ulf Friederichs, Düsseldorf (CH)

(73) Assignee: Qiagen GmbH, Hilden (DE)

( * ) Notice: Subject to any disclaimer, the term of this patent is extended or adjusted under 35 U.S.C. 154(b) by 0 days.

(21) Appl. No.: 10/204,735

(22) PCT Filed: Feb. 19, 2001

(86) PCT No.: PCT/EP01/01854

§ 371 (c)(1),
(2), (4) Date: Dec. 9, 2002

(87) PCT Pub. No.: WO01/62386

PCT Pub. Date: Aug. 30, 2001

(65) Prior Publication Data

US 2003/0146139 A1 Aug. 7, 2003

(30) Foreign Application Priority Data

Feb. 22, 2000 (DE) .......................... 100 08 023

(51) Int. Cl.$^7$ .............................. B01D 61/16; B01L 3/00
(52) U.S. Cl. .................. 210/181; 210/184; 210/188; 210/258; 159/DIG. 16
(58) Field of Search .................. 210/143, 175, 210/181, 184, 188, 258; 159/DIG. 16; 202/91

(56) References Cited

U.S. PATENT DOCUMENTS

| | | |
|---|---|---|
| 5,137,604 A | 8/1992 | Meeks et al. |
| 5,645,723 A | 7/1997 | Fujishiro et al. |
| 5,772,851 A * | 6/1998 | Barwich et al. ............... 203/49 |
| 5,772,900 A | 6/1998 | Yorita et al. |

FOREIGN PATENT DOCUMENTS

| | | |
|---|---|---|
| GB | 2 280 430 | 2/1995 |
| WO | WO 98/53912 | 12/1998 |

* cited by examiner

*Primary Examiner*—Fred G. Prince
(74) *Attorney, Agent, or Firm*—Leon R. Yankwich; Michael R. Wesolowski

(57) ABSTRACT

The invention relates to a device for processing, especially for filtering and removing, fluids and fluid remnants in a low-pressure chamber (1). The device comprises a vacuum pump (30) and a separator (16), whereby the low-pressure chamber is connected to the separator via a first line (10), and the low-pressure chamber is connected to the vacuum pump via a second line (20) so that the low-pressure chamber can be evacuated while bypassing the separator. The invention also relates to a low-pressure chamber for processing fluids which is equipped with a heating plate with holes for heating areas of the interior space of the low-pressure chamber.

30 Claims, 9 Drawing Sheets

DEVICE FOR FILTERING AND REMOVING FLUIDS

This application is a United States national phase filing under 35 U.S.C. §371 of international (PCT) application No. PCT/EP/01/01854, filed Feb. 19, 2001, which claims priority to German Application No. 100 08 023.5, filed Feb. 22, 2000.

TECHNICAL FIELD

The invention relates to apparatus and a process for automatically filtering and eliminating liquids and liquid residues in a vacuum chamber.

BACKGROUND OF THE INVENTION

In numerous technical fields, particularly chemistry, biology and environmental sciences, it is necessary to analyse liquids, break them down into their components or react them with other substances. For this purpose liquids are filtered, dried, washed, pipetted and subjected to other treatment, the term liquid basically meaning any substance which occurs in liquid form or which is found in a liquid. The treatments often consist of a long series of treatment procedures, which means that it is necessary to automate these procedures using robots.

Thus, for example the "BioRobot 9600" produced by the present Applicant has been on the market for some years, for automatically carrying out molecular biological processes such as, for example, the filtering, washing and eluting of nucleic acids or the isolation of RNA and/or DNA. Support members known as filter modules are used for these processes, comprising a plurality of containers arranged in a matrix form. These containers have an inlet aperture at the top and an outlet aperture at the bottom. The containers also contain filter bodies in the form of suitable membranes or filters which are suitable for binding the substances which are to be analysed in the liquid samples.

Thus, for example, in order to produce highly purified DNA plasmids using an individual pipetting device, first of all cell cultures are put into suspension, lysed and then placed in the containers on the support plate by means of a pipetting device. Then the carrier plates holding the filled containers are placed on a vacuum chamber so that the outlet apertures of the containers project into the vacuum chamber. By applying negative pressure in the negative pressure chamber the liquids in the containers are sucked through the filter bodies into the negative pressure chamber. The constituents to be analysed together with other components of the liquid samples remain suspended in the filter bodies. In order to recover the desired components of the liquid samples, the unwanted substances first have to be washed out of the filter bodies. To do this, washing solutions of different concentrations are pipetted into the containers. Using these washing solutions, some of the unwanted components of the liquid samples are detached from the filter bodies. Then the ingredients of interest are released from the filter bodies using an eluant solution and collected.

The solutions used in the individual steps may, however, contaminate the solution used in the next step. Thus, for example, after a washing step, drops of liquid wash solution may form on the outlet apertures of the containers and have to be removed before the following elution step. Previously, the carrier members or microtitre plates were dropped manually onto a substrate of absorbent material to shake off these drops. As described in WO 98/53912, the removal of the residual liquid was automated by the application of a vacuum.

In this apparatus the liquids sucked through the filters usually flowed to a separator, under the effect of gravity. There. the liquid was collected so that it could be re-used and/or examined as necessary. However, liquid residues particularly in the region of the filter body or on the outlet apertures of the containers could not be eliminated by this method, or only very slowly. The drying process of the filter bodies and outlet apertures of the containers therefore takes a long time or is not completed. However, it has been found that liquid residues have to be removed as completely as possible as they affect the purity of the filter residues in the containers which are to be analysed, which are usually only present in small amounts, and alter their chemical characteristics.

DESCRIPTION OF THE INVENTION

The problem of the invention was therefore to provide an apparatus which makes it possible on the one hand to filter liquids with negative pressure and to collect the filtered liquids but on the other hand also to eliminate liquids, particularly liquid residues in the region of the filter body or on the outlet openings of the containers as completely as possible within a short time, so as to solve the known problems of the prior art.

To solve this problem, an apparatus is proposed for treating liquids in a negative pressure chamber with a vacuum pump and a separator, the negative pressure chamber being connected to the separator by a first line and a first closure device being arranged between the negative pressure chamber and separator, while the negative pressure chamber is connected to the vacuum pump via a second line, so that the negative pressure chamber can be evacuated while avoiding the separator.

Is It has been found that, for example, the filter body stores a relatively large amount of liquid by its capillary action, which is not eliminated by means of the vacuum applied. These liquids may also be eliminated by evacuating the negative pressure chamber while avoiding the separator.

By liquids is meant basically any substance which is present in liquid form or which is found in a liquid. This means, in particular, chemical and/or biological samples or chemical and/or biological samples contained in liquids and the substances needed for treating chemical and/or biological samples.

By the treatment of liquids in a negative pressure chamber are meant various activities relating to liquids and/or liquid residues in a negative pressure chamber, such as for example drawing a liquid through a filter, eliminating liquid residues by pumping out or evaporation, which may preferably be referred to as the drying of the negative pressure chamber, as well as collecting liquids in a container or releasing liquids to flow into a separator.

By the separator is meant in particular an apparatus which is able to catch liquids and collect them in a separating vessel. The separating vessel may preferably be large enough to hold some 100 ml of liquid. This collection is achieved, for example, by placing the separator underneath the liquid which is to be collected, so that the liquid flows or falls by gravity into a separation vessel; alternatively, the liquid may also be caught by material structures which oppose the flow of liquid produced by a vacuum pump, for example, so that the liquid is deposited on the material structure and flows or falls into the separation vessel. In a preferred embodiment the separator consists of a sealed separation vessel which has two tubes coming from above which project openly into the separation vessel. One of the tubes is a feed tube through which the liquid is transported by gravity and/or suction by a vacuum pump into the separation vessel and collected therein; the other tube is the outlet pipe to which a vacuum pump is connected. The outlet pipe ends above the level of the liquid, so that the liquids collected in the separation vessel cannot reach the vacuum pump. Preferably, the opening of the outlet pipe is above the opening of the inlet pipes. However, other methods of separating liquids may preferably be used. It is also possible to mount a plurality of separators in various arrangements on the negative pressure chamber or on the pipes.

The evacuation of the negative pressure chamber without a separator is carried out using one (or more) vacuum pumps which are connected to the negative pressure chamber, the separator being separated from the negative pressure chamber or the vacuum pump. The separation is expediently achieved by means of a closure device. By a closure device is meant, for example, a device with an input and output, which can be switched between the throughflow and blocking positions. Preferably, the closure device is a vacuum-tolerating blocking valve. If the separator is separated from the negative pressure chamber in such a way that there are no very great liquid reservoirs in the negative pressure chamber connected to the negative pressure chamber, a high negative pressure can rapidly be achieved with the vacuum pump which evaporates the remaining liquid residues more quickly.

When the separator is connected to the negative pressure chamber the known apparatus can convey liquids into the separator and, when the separator is disconnected from the negative pressure chamber, the negative pressure chamber and other devices provided therein are freed from liquid residues.

In another embodiment according to the invention the apparatus has a first line which connects the negative pressure chamber to a first vacuum pump via the separator. The pump assists the transporting of the liquids into the separator.

Advantageously, a closure device which may in turn be a vacuum-tolerating blocking valve may be arranged between the separator and negative pressure chamber and preferably also between the separator and vacuum pump. The negative pressure chamber, including the separator, can be pumped out through the first line. If the separator is filled with liquid, the evacuation process goes slowly, as the liquid in the separator continues to yield gas as a result of evaporation for a long time. As long as the liquid in the separator is not totally evaporated, no high negative pressure can be achieved either. This is avoided by means of the closure device.

According to another embodiment the apparatus has a second line which connects the negative pressure chamber to a second vacuum pump. As there is no liquid-filled separator in the line in this case, the negative pressure chamber can quickly be evacuated and the liquid residues rapidly eliminated through this line, with the same pumping power, provided that the separator is separated from the negative pressure chamber by the closure device. Preferably, the second line also has at least one closure device which ensures that no liquid passes from the negative pressure chamber into the vacuum pump in the filtering process.

Preferably, only one vacuum pump rather than two is used for the apparatus, to save money and weight. The first line between the separator and vacuum pump and the second line are preferably combined into one line by a T-shaped pipe section before they open into the intake connector of the vacuum pump. Preferably, the first line between the separator and negative pressure chamber and the second line are also joined together by a T-shaped pipe section , so as to open into the negative pressure chamber with one line.

Preferably, the first and second closure devices are replaced by a 3/2-way valve to reduce the number of active components that have to be actuated. The 3/2-way valve is incorporated in the piping system so that the input of the 3/2-way valve is connected to the negative pressure chamber, while the first of the two outlets of the 3/2-way valve leads to the separator and the second outlet leads directly to the vacuum pump. Advantageously, the 3/2-way valve replaces two connections to the negative pressure chamber or the first T-shaped pipe section . The 3/2-way valve can be switched into two switch positions; in the first position it connects the inlet to the first outlet and blocks the second outlet, while in the second switching position it connects the inlet to the second outlet and blocks the first outlet.

In another embodiment of the invention the additional first and additional second closure devices are advantageously replaced by another 3/2-way valve in order to reduce the number of active components to be actuated. The additional 3/2-way valve is preferably incorporated in the pipe system in such a way that the inlet of the additional 3/2-way valve is connected to the vacuum pump, while the first of the two outlets of the additional 3/2-way valves leads to the separator and the second outlet leads past the separator to the negative pressure chamber. This makes it possible to use a vacuum pump. Advantageously, the additional 3/2-way valve also replaces the second T-shaped pipe section . The 3/2-way valve can preferably be switched into two switching positions; in the first position it connects the inlet to the first outlet and blocks the second outlet, while in the second switching position it connects the inlet to the second outlet and blocks the first outlet.

In another preferred embodiment the device is a device for filtering liquids in a negative pressure chamber. The vacuum in the negative pressure chamber preferably serves to suck liquids which have been poured into the inlet openings of the containers with filter bodies through said filter bodies. The negative pressure chamber is preferably arranged for this purpose so that it has an opening at the top into which one or more of these containers with liquids to be filtered can be placed in the negative pressure chamber. The top opening of the negative pressure chamber and the containers are arranged so that the container and top opening form a gastight seal with one another. As long as there is liquid above the filter body in the container, the negative pressure chamber is still sealed off in gastight manner, so that a vacuum pump can produce a negative pressure in the negative pressure chamber. This negative pressure sucks the liquids housed in the containers through the filter bodies, to allow rapid filtering. Only when all the liquid in the containers has been sucked through the filters and the filtering is thus complete can atmospheric air enter the negative pressure chamber through the filters.

Filtering is to be understood in the wider sense: it means the suction of liquids in specified containers through the filter bodies by means of a negative pressure, while this process also takes place when washing filter residues with a solution, particularly ethanol, or when eluting filter residues with an eluant solution.

During filtering, the closure devices, particularly the blocking valves and/or the 3/2-way valves of the lines are preferably switched over so that the separator is connected to the negative pressure chamber and the negative pressure chamber is evacuted together with the separator. The liquid sucked through the filter bodies thus flows to the separator, assisted by gravity or pump suction. Care must be taken to ensure that no liquid gets into the vacuum pump as a result of suction or gravity. To prevent this, either it is preferably pumped through the separator, so that the liquid is caught therein, or the inlet of the pump connector in the negative pressure chamber is located at a point which the liquids cannot get to, even when sucked in by the pumping action. The two 3/2-way valves are preferably both switched to the first switching position so that evacuation is carried out with the separator.

According to another aspect the apparatus is an apparatus for eliminating liquids, particularly liquid residues, which have not flowed into the separator during filtering but have remained in the filter bodies or are left suspended as droplets on the outlets of the containers or have remained on the surfaces inside the negative pressure chamber. As these liquid residues, particularly in the filter bodies, can falsify an analysis, they must be reduced to a minimum. Preferably, the boiling temperature of the liquid is lowered with the aid of negative pressure by means of a vacuum pump connected to the negative pressure chamber, so that the liquid is evaporated faster. To maximise the negative pressure, a lid is preferably placed on the negative pressure chamber, sealing off the top opening of the negative pressure chamber in gastight manner as otherwise the chamber would be open. The gas is sucked out by means of the vacuum pump.

The liquids are also eliminated by the fact that closure devices and valves are used to separate the separator from the negative pressure chamber, and a vacuum pump which is not connected to a separator evacuates the negative pressure chamber. As the separator therefore cannot constantly supply new gas from evaporating liquid to the negative pressure chamber, the negative pressure in the chamber can be increased and hence the boiling temperature of the liquid residues can be further lowered. As a result, the residual liquid is evaporated faster and more completely. Total elimination of the residual liquids is particularly essential in the containers and filter bodies, as these often contain small amounts of substances to be analysed, which would be contaminated by residual fluids and would therefore give false results. To eliminate the liquids the two 3/2-way valves are switched to the second switching position, so that evacuation is carried out without the separator.

According to another embodiment, a ventilating valve is advantageously connected to the negative pressure chamber or at some other suitable point, so that the negative pressure chamber can be ventilated. Ventilation is carried out, for example, after a step for eliminating liquids, as a repeated cycle of pumping out and ventilation has proved advantageous for the elimination of liquids. Conveniently, a throttle valve is provided between the ventilation valve and the negative pressure chamber, to avoid an excessively rapid rise in pressure during ventilation, which would damage the negative pressure chamber or the liquids in the negative pressure chamber or cause them to be churned up. Preferably, a pressure sensor is mounted on the negative pressure chamber or on one of the lines, to monitor the pressure in the negative pressure chamber.

Preferably, the apparatus comprises a central control for closure devices and blocking valves, 3/2-way valves, ventilation valve and/or vacuum pumps. This control can be used to monitor the apparatus and operate it comfortably. In particular, processes such as filtering, the removal of liquid and ventilation can be more easily automated, repeated reproducibly and thus optimised Incorrect operation also hardly ever occurs with fully automated processes.

According to another aspect a negative pressure chamber according to claim 16 is provided. This is used for treating liquids and particularly for use with an apparatus as described above. The negative pressure chamber has a hotplate for heating up areas of the negative pressure chamber. Preferably, the hotplate is arranged in the bottom part of the negative pressure chamber. More preferably, the hotplate has holes.

Preferably, the negative pressure chamber may hold containers with which filtering can be carried out as claimed in claim 9. The containers preferably have an inlet opening, filter body and an outlet opening, so that liquids introduced through the inlet opening can pass through the filter to the outlet opening under the effect of gravity or vacuum suction. Preferably, these containers are arranged in a matrix-like structure on a carrier plate, so that multiple filtering can preferably be carried out in parallel. The holes in the hotplate are preferably shaped so that the lower portion of the containers are able to project into the holes. The hotplate with the holes preferably thus heats the containers in the region of the filter body and at the outlet region and thus contributes to the accelerated elimination of liquid residues in the filter region and outlet region. In this way the chemical and/or biological substances, particularly nucleic acids, which have accumulated in the filter bodies can be isolated quickly and with a high degree of purity. Preferably, the hotplate can also help to control the temperature of the liquids to be analysed in the containers. Moreover, this avoids the spraying of liquid onto the top of the hotplate and reduces the possibility of cross-contamination.

Preferably, the hotplate is heated by a heating strip arranged in the outer part of the hotplate. In a preferred embodiment, the heating strip is arranged around the hotplate. The hotplate is preferably made of a heat-conducting material, so that the temperature is distributed as uniformly as possible over the entire surface.

According to another embodiment, the negative pressure chamber has at least one heating element in the region of the side walls. The heating element serves to heat up the side walls as necessary, thereby advantageously preventing the condensation of liquids and liquid residues on the side walls which are cooler by comparison with the hotplate and filter bodies. The heating element may preferably also serve to heat up the liquids in the containers. The heating element is preferably a heating strip which is preferably mounted in the inner wall of the negative pressure chamber.

Preferably, at least one temperature sensor is mounted in the negative pressure chamber, for reading off the temperature in said chamber. Preferably an electronic unit controls the temperature on the hotplate and/or the heating elements, which is advantageous for gentle treatment of the liquids and the fastest possible drying process. The electronic control of the hotplate and/or heating element is also useful for automated operation of heating cycles.

A process for eliminating liquids in a negative pressure chamber is also proposed, having the following steps:
 a) the negative pressure chamber is sealed off to be airtight;
 b) the negative pressure chamber is connected to the vacuum pump and the separator is separated off;
 c) the vacuum pump is switched on and the negative pressure chamber is pumped out.

Preferably, the negative pressure chamber is sealed off to be airtight, to ensure the best possible negative pressure, thereby significantly speeding up the elimination of the liquid residues. Preferably, the process is used to dry the filters with the filter residues which are to be analysed, i.e. if the containers are arranged inside the negative pressure chamber. To seal off the negative pressure chamber with the containers arranged therein in gastight manner, a lid which covers the containers and forms a gastight seal with the opening in the negative pressure chamber is preferably placed on the negative pressure chamber.

Preferably, the negative pressure chamber is connected to a vacuum pump and the separator is separated from the negative pressure chamber and vacuum pump. The vacuum pump is then preferably switched on. The absence of the separator from the negative pressure chamber which is to be evacuated improves the vacuum, as no evaporating liquid can escape from the separator into the negative pressure chamber which is to be evacuated. This significantly increases the rate at which the liquids to be eliminated can be evaporated and pumped out.

The negative pressure chamber is preferably ventilated after a period of pumping. This step is preferably carried out when the elimination of the liquids is to be speeded up by a cycle of to pumping and ventilation which is to be repeated several times.

Preferably, ethanol which is a preferred washing solution for nucleic acids and for isolating liquids containing DNA or RNA is eliminated in the process.

Preferably, to eliminate the liquids, the negative pressure chamber is heated by means of heating elements or the hotplate in order to speed up the evaporation. It is preferably heated to a temperature above the boiling point, which ensures the fastest possible elimination of the liquids. Since the boiling point of a liquid falls as the negative pressure increases, a good vacuum enables the liquid to boil even at low temperatures.

The process is preferably controlled by an electronic unit, as this makes it possible to achieve optimum, reproducible adjustment of the temperature in the negative pressure chamber, the duration of pumping and the ventilation times as well as the heating temperatures to be selected in the negative pressure chamber, and to automate the process.

BRIEF DESCRIPTION OF THE DRAWINGS

The drawings show embodiments of the invention by way of example. In the drawings are shown.

EMBODIMENTS OF THE INVENTION

Figure 1:
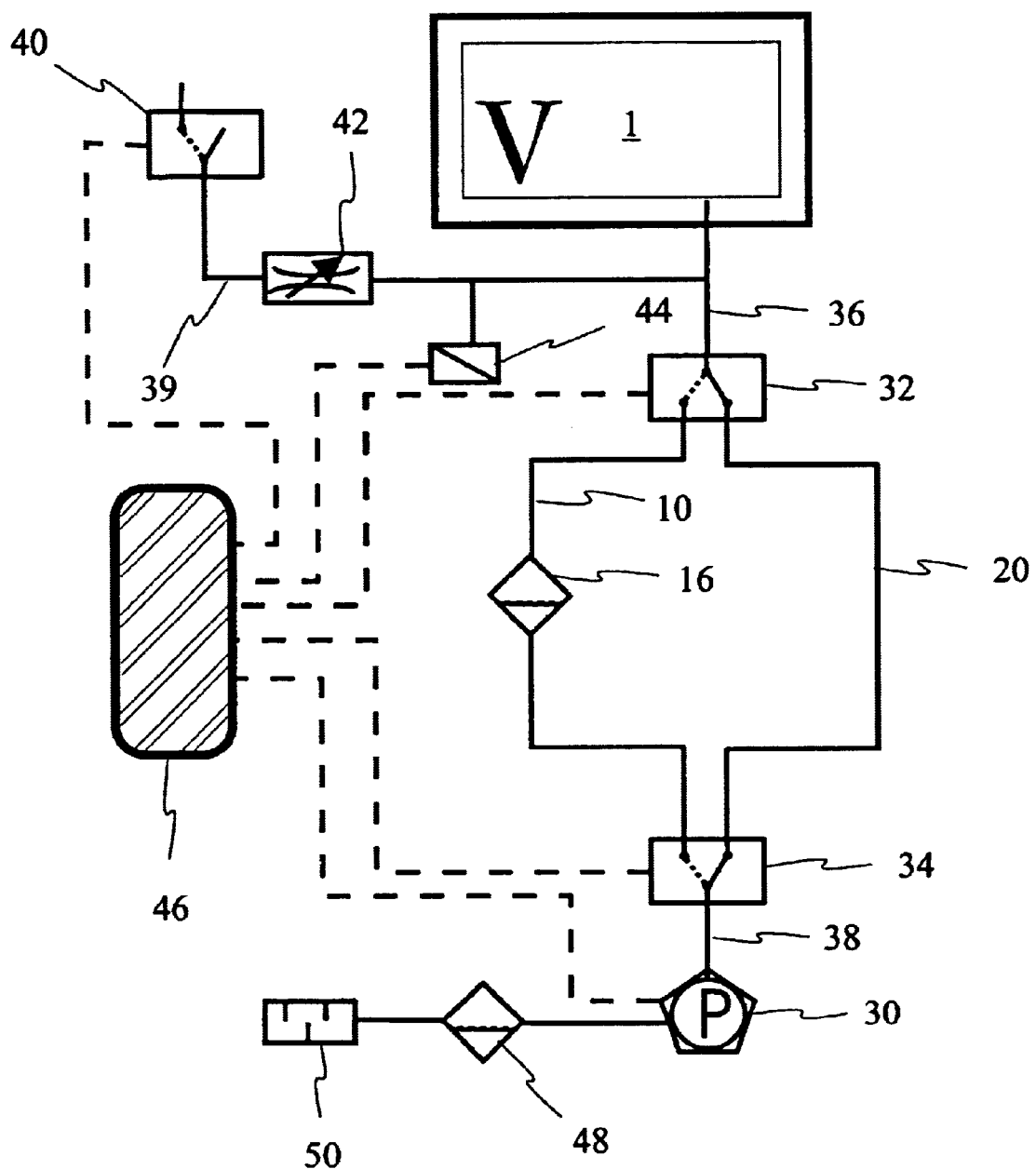
FIG. 1 The construction of the apparatus according to the invention for treating liquids in the negative pressure chamber, particularly for filtering and eliminating liquids in the negative pressure chamber under electronic control.

FIG. 1 diagrammatically shows a preferred embodiment of the apparatus for treating liquids in a negative pressure chamber, particularly for filtering and eliminating liquids. The essential elements are the negative pressure chamber 1, the separator 16, the vacuum pump 30 and the 3/2-way valve 32 and the additional 3/2-way valve 34. If both 3/2-way valves are switched to the first switching position the vacuum pump 30 is connected to the negative pressure chamber solely via the separator 16. If both 3/2-way valves are switched to the second switching position, the vacuum pump 30 is connected solely to the negative pressure chamber, avoiding the separator.

Other elements of the embodiment shown are a ventilation line 39 with a ventilation valve 40 and preferably a throttle valve 42 between the ventilation valve 40 and negative pressure chamber 1. The throttle valve can be used, for example, to adjust the speed at which the ventilation of the negative pressure chamber is to proceed. In the embodiment shown there is also a pressure sensor 44 which is connected to the ventilation line. The pressure sensor 44 measures and monitors the pressure prevailing in the negative pressure chamber 1. Basically, it does not matter how long the ventilation line is or where it opens into the negative pressure chamber. With a suitable structure, a ventilation line may possibly be omitted altogether if it is possible to mount the ventilation valve and/or throttle valve and/or pressure sensor directly on the negative pressure housing. What is critical is that the ventilation valve is able to ventilate the negative pressure chamber and the pressure in the negative pressure chamber can preferably be measured by means of the pressure sensor.

Moreover, another separator 48 and a silencer 50 are shown behind the vacuum pump 30. The additional separator 48 has the function of removing moisture from the air emitted by the pump and optionally filtering the air released at the back of the vacuum pump.

Finally, the electronic regulating means 46 is shown, which reads and/or regulates the active components of the system, particularly the 3/2-way valves, ventilation valve, pump and pressure sensor. However, the electronic regulating means 46 are not restricted to the components shown; thus, the control unit may also be used to regulate the temperature in the negative pressure chamber or to allow the lid 66 to be raised from or set down on the negative pressure chamber. Using the electronic control means it is thus possible to automate and optimise the liquid treatment procedure, i.e. a filtering or drying procedure carried out one after the other, for example. This not only saves time but ensures that the operation is as reproducible as possible and free from errors.

FIG. 1 shows a preferred embodiment of the apparatus for treating liquids in a negative pressure chamber. By switching the two 3/2-way valves to the first switching position a negative pressure can be created in the negative pressure chamber 1 which is used for the filtering, for example, and the liquid can be passed to the separator 16.

Figure 9:
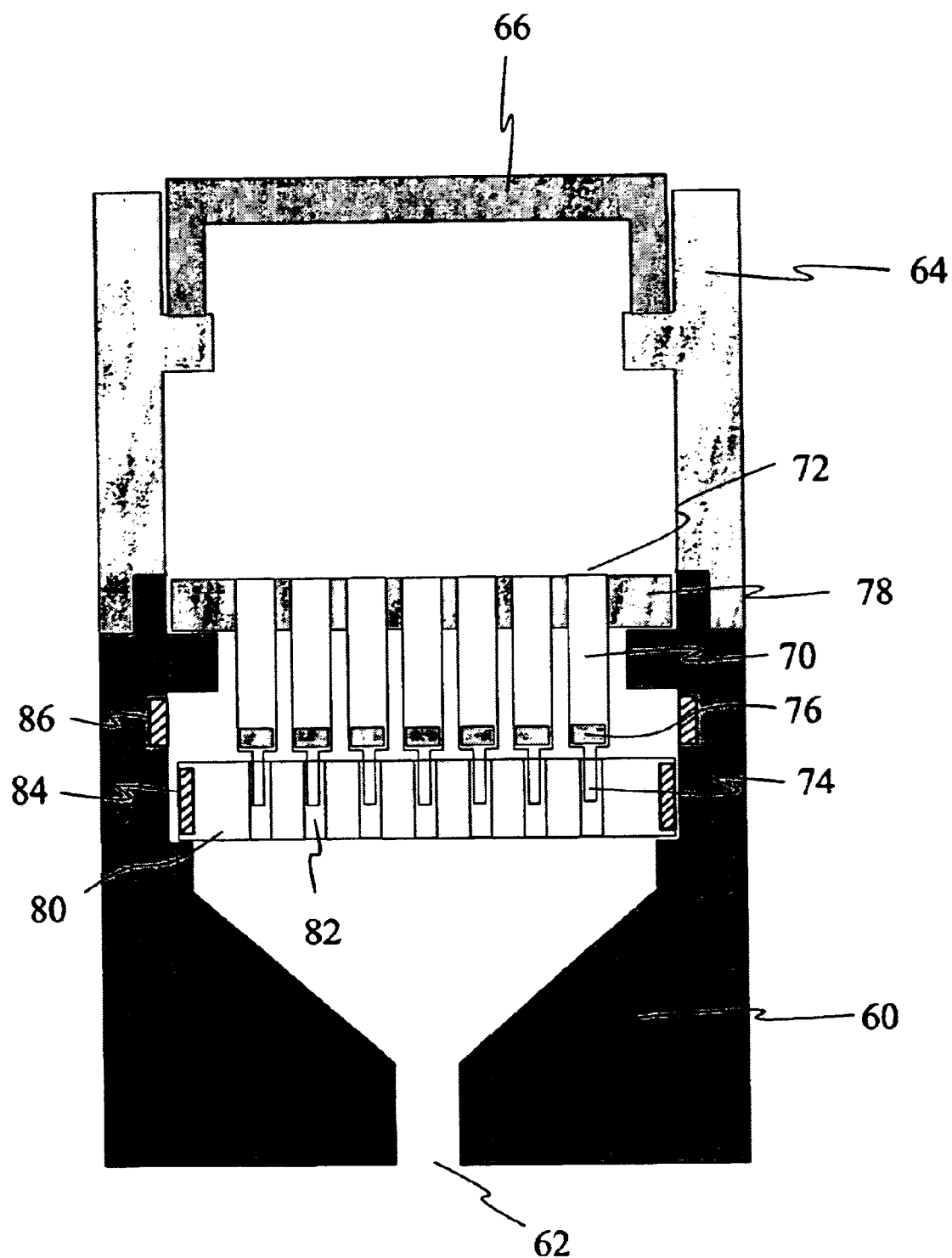
FIG. 9 A preferred embodiment of a negative pressure chamber for treating liquids, particularly for filtering, washing and drying liquid samples.

If both 3/2-way valves in FIG. 1 are switched to the second switching position, it is impossible for any very great amounts of liquid to be received, as the liquids could then easily reach the vacuum pump 30 and damage it. However, this switching position is intended for eliminating liquid residues or for drying the negative pressure chamber 1. In this switching position the separator 16 is separated from the negative pressure chamber , which makes evacuation considerably easier, as no evaporated liquid can pass from the separator 16 into the negative pressure chamber 1. Moreover (as shown in FIG. 9) in a preferred embodiment, in this switching position, the cover 66 is fitted onto the negative pressure housing in gastight manner, so that the negative pressure chamber is sealed off in gastight manner, apart from the outflow 62. In the embodiment described, the pressure can thus be reduced to about 30 mbar, for example, which is an order of magnitude better than when evacuation is done with the separator attached. As a result of the reduced pressure thus obtained, the boiling point of liquids falls, so that the liquid residues remaining on the filter bodies 76 of the containers 70 or on other surfaces in the negative pressure chamber after filtering, for example, can evaporate substantially faster and be pumped away by the vacuum pump 30. The better drying leads directly to better results if, for example, it is important to obtain the filter residues in the purest possible form: for example, by more complete elimination of the ethanol washing solution in the washing process for isolating nucleic acids it is possible to obtain a residual ethanol content in nucleic acids of less than 0.5%.

Figure 2:
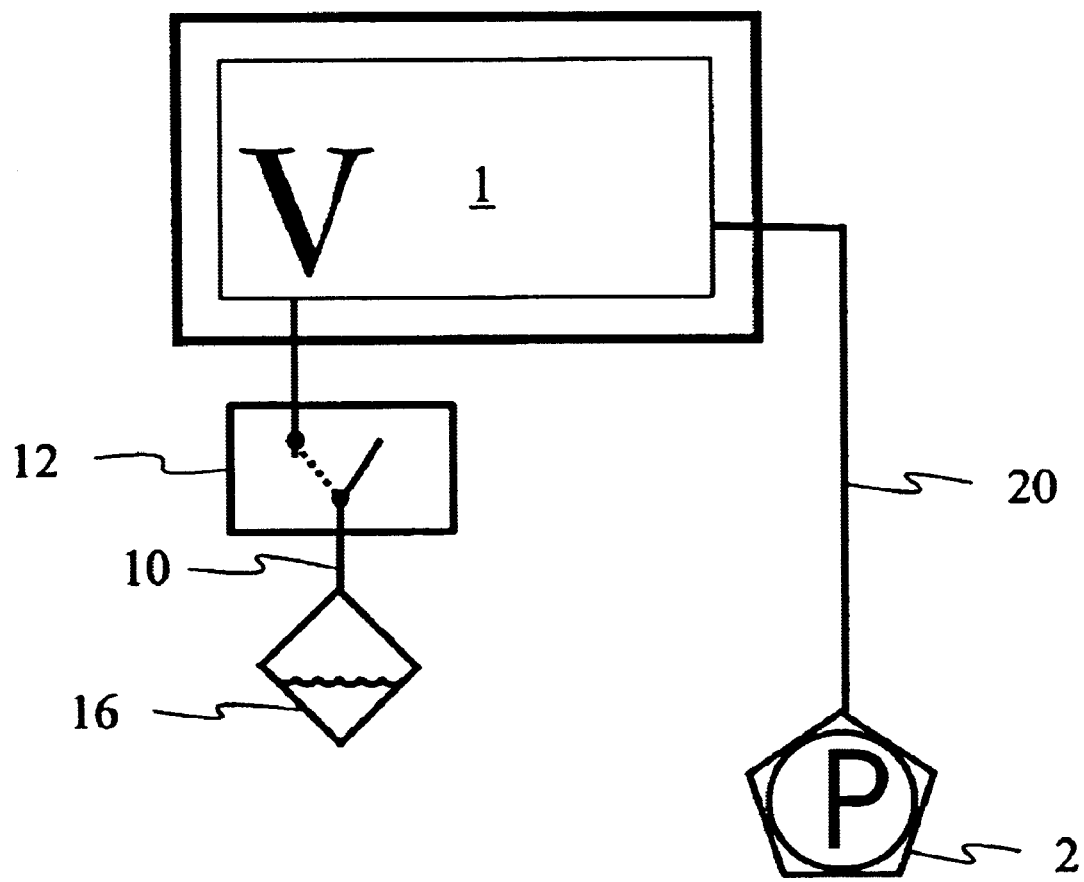
FIG. 2–FIG. 8 Other embodiments according to the invention of the apparatus for treating liquids in the negative pressure chamber, particularly for filtering and eliminating liquids in the negative pressure chamber.

FIG. 1 is a preferred embodiment of the apparatus according to the invention. Other embodiments are shown in FIGS. 2 to 8. FIG. 2 shows an embodiment with minimal construction, with which filtering can be carried out with negative pressure and drying can be done while avoiding the separator. If the first closure device 12 is switched to throughflow, filtered liquid is able to flow, by gravity, into the separator 16 provided underneath the filter bodies. The negative pressure for the filtering is provided by the vacuum pump 2, which is connected by a line 20 to the negative pressure chamber 1. In this construction care must be taken to protect the line 20 from the liquids passing through the filter bodies to ensure that no liquid can get into the vacuum pump.

It should be mentioned here, referring to all the other diagrammatic FIGS. 1 to 8, that these Figures do not determine the geometric manner in which the first line 10 and the second line 20 are connected to the negative pressure chamber. They may be connected side by side or laterally to the negative pressure chamber or they may be combined, for example, by means of a T-shaped pipe section and then connected to the negative pressure chamber. The line leading to the separator is generally connected to the base of the negative pressure chamber, so as to remove the liquids accumulating on the bottom. Preferably, the base of the chamber is conically convergent in shape, to promote the outflow of the liquids. In this case, the outlet is preferably provided at the lowest point. A second outlet provided on the bottom is then technically more complex to produce. The second outlet, particularly the one for the vacuum pump 2, can then advantageously be provided on the side, to make it difficult for the liquid to enter this line. When attaching the first line 10 and second line 20 the only factor to bear in mind is that the apparatus is not subjected to any restrictions in its function.

If the negative pressure chamber 1 is to be freed from liquid residues, the blocking device 12 is closed and preferably a lid is placed on the negative pressure chamber to form a gastight seal. As described in FIG. 1 the negative pressure chamber can then be pumped out under significantly better negative pressure values, so that the liquid residues can evaporate and be pumped out faster. There are no particular restrictions on the choice of closure device 12 here or in any of the other Figures; preferably, the closure device is a vacuum-tolerating blocking valve which reacts with resistance to chemical attacks. With the simplicity of this construction, a major disadvantage of this embodiment is that the separator has to catch and collect the liquid without the assistance of the vacuum pump. There is also a danger that in spite of all the precautions the vacuum pump will be contaminated with liquids, as it cannot be protected from the liquids by a barrier.

Figure 3:
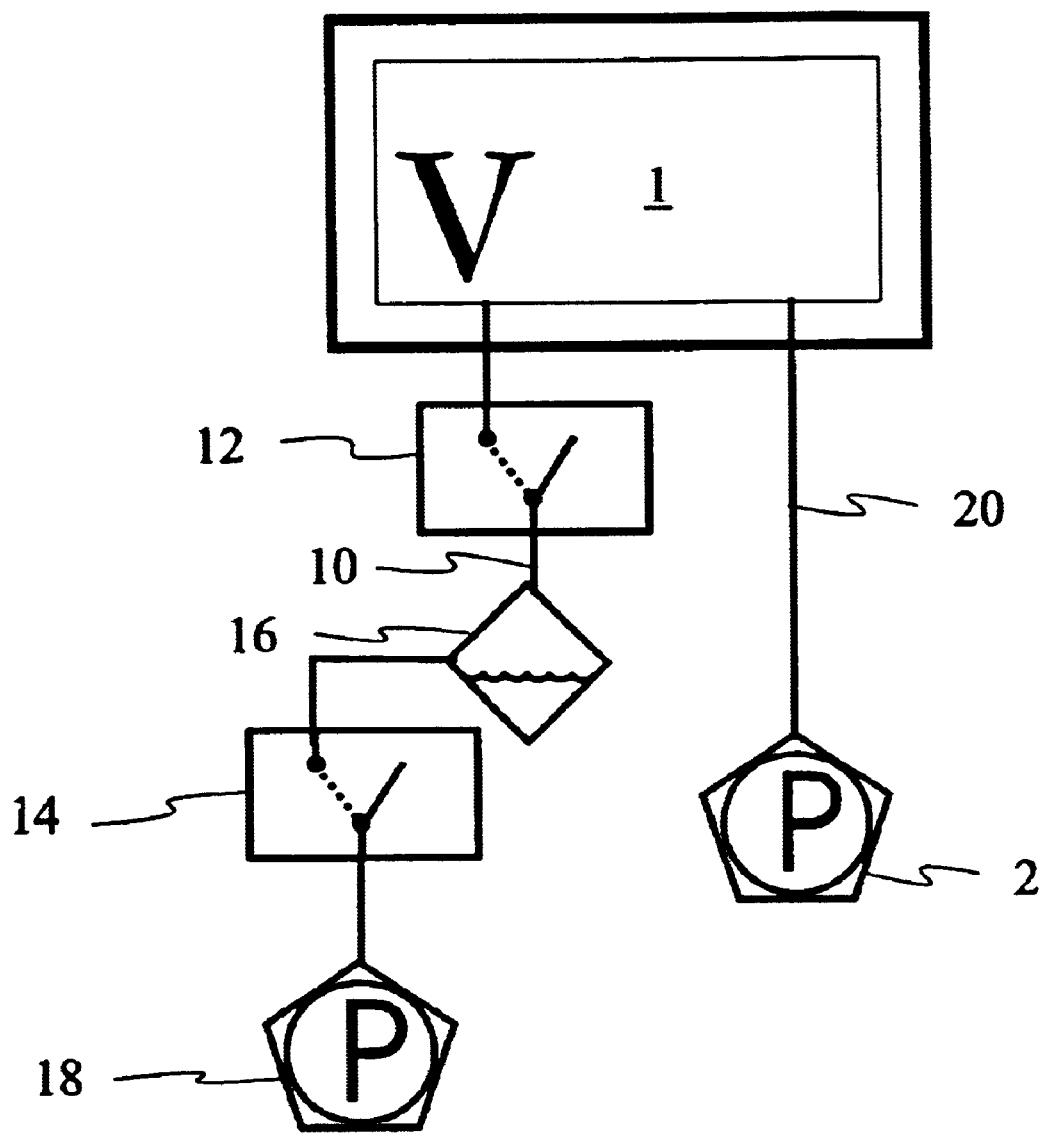

FIG. 3 shows an embodiment of the apparatus which is expanded, compared with FIG. 2, by an additional first closure device 12 and an additional pump 18, which is connected to the separator 16. This apparatus has the advantage, over the apparatus in FIG. 2, that the additional vacuum pump 19 and not the unprotected vacuum pump 2 provides the necessary negative pressure for the filtering. Thus, the vacuum pump 2 may be switched off during the filtering, thereby reducing the risk of damage to the pump caused by the ingress of liquid. Advantageously, the connection for the second line is provided on the side of the negative pressure chamber to give the pump even greater protection from penetrating liquids. Another advantage of this embodiment is that the additional vacuum pump 18 assists the separator with additional suction during the catching and collection of the liquid.

Figure 4:
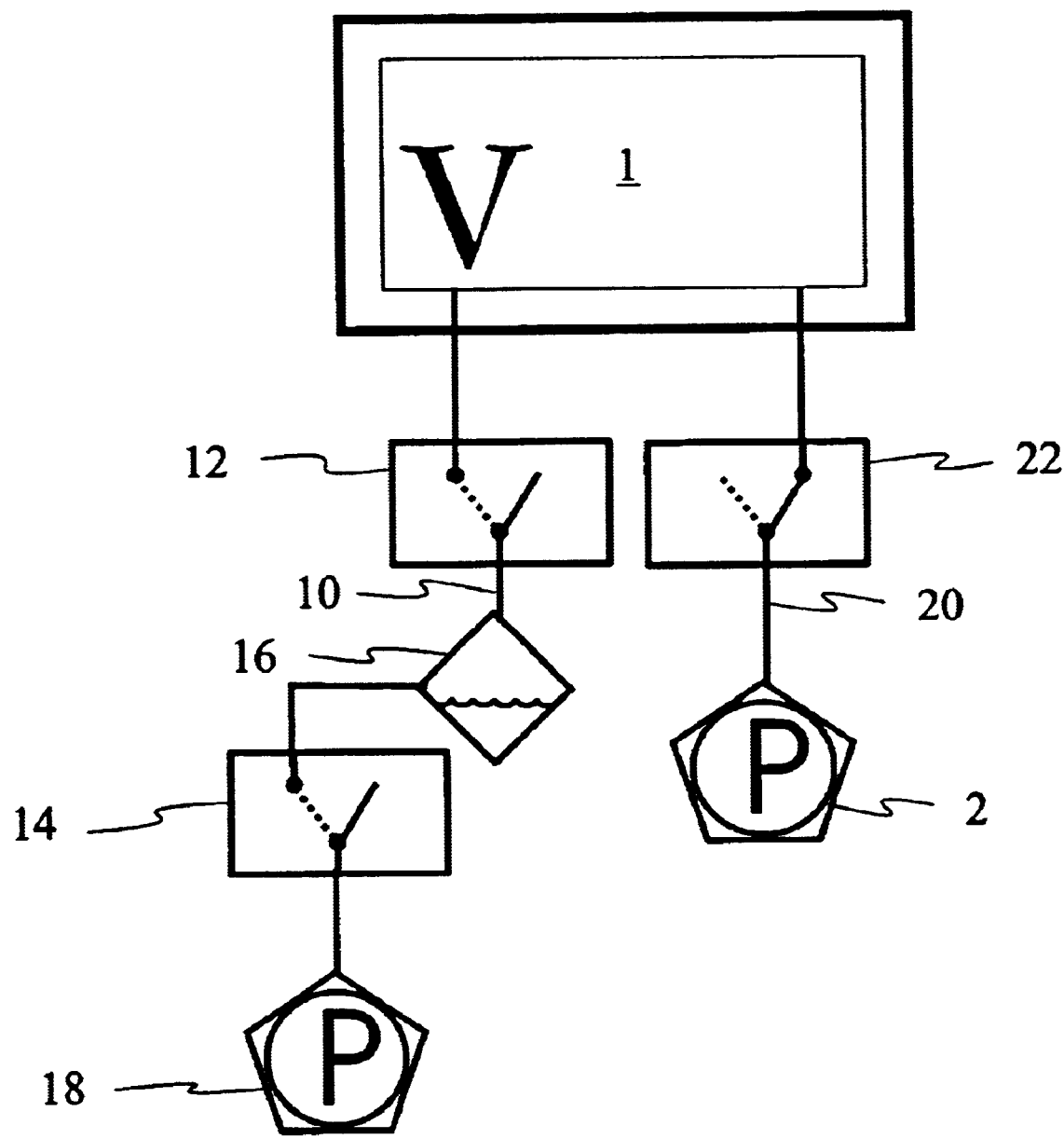

The embodiment according to FIG. 4 differs from that in FIG. 3 by a second closure device 22 which is incorporated between the vacuum pump 2 and the negative pressure chamber 1. The closure device can protect the vacuum pump 2 from the moisture which might otherwise get into the line 20 and possibly destroy the pump during the filtering. Preferably, the blocking valve is mounted where the line 20 opens into the negative pressure chamber, so that when the closure device is closed the liquid which has accumulated there can flow back into the negative pressure chamber before the closure device is reopened, e.g. for drying.

Figure 5:
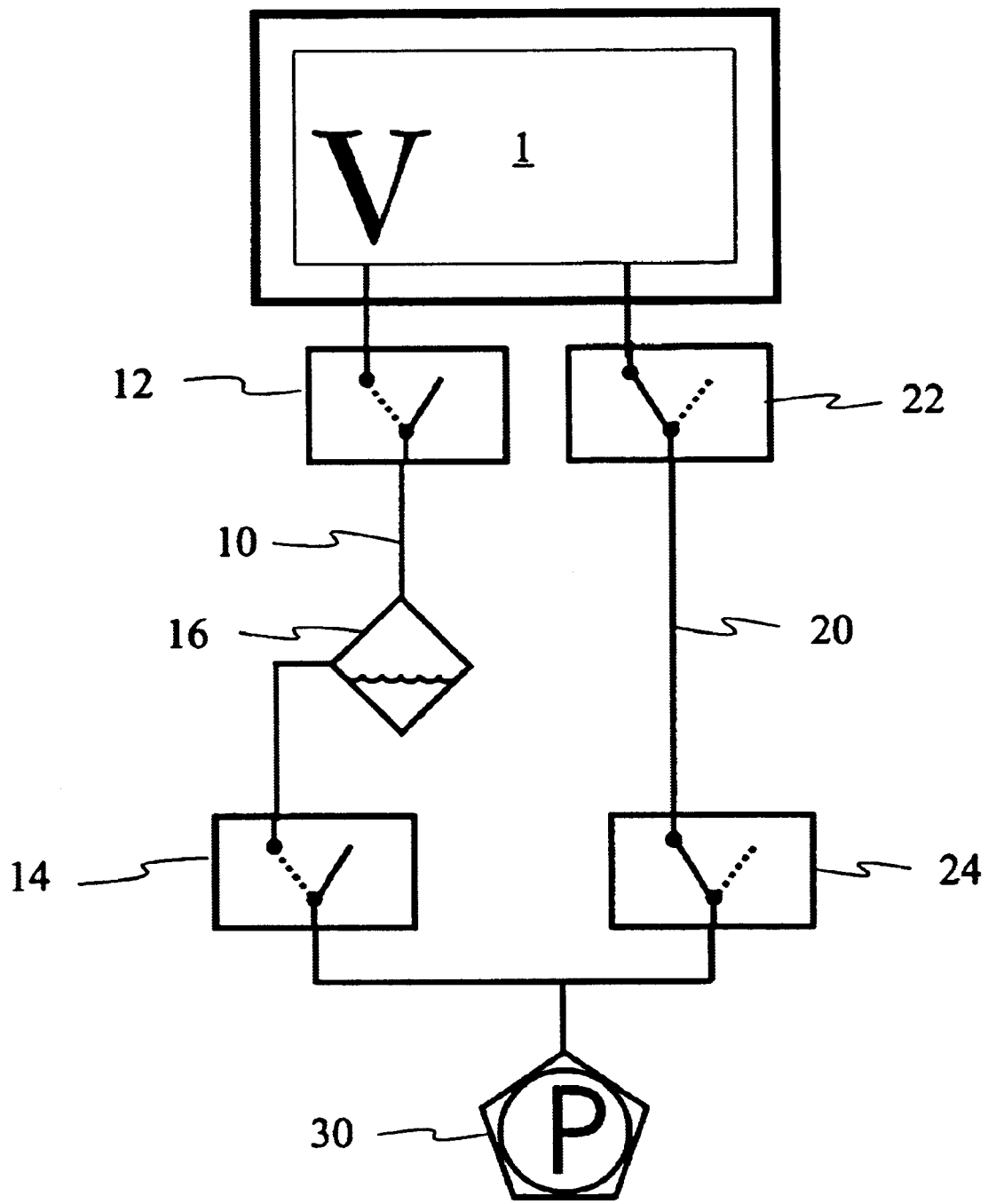

FIG. 5 differs from FIG. 4 on the one hand by an additional second closure device 24 and by the fact that the vacuum pump 2 and the additional vacuum pump 18 are replaced by a vacuum pump 30. This may be achieved, for example, by means of a T-shaped pipe section with which the two lines 10 and 20 are combined in order to enter the vacuum pump with a joint lower line 38. However, other embodiments are also possible. This construction does away with the need for a vacuum pump in the apparatus, saving on costs, weight, noise and complexity of construction.

Figure 6:
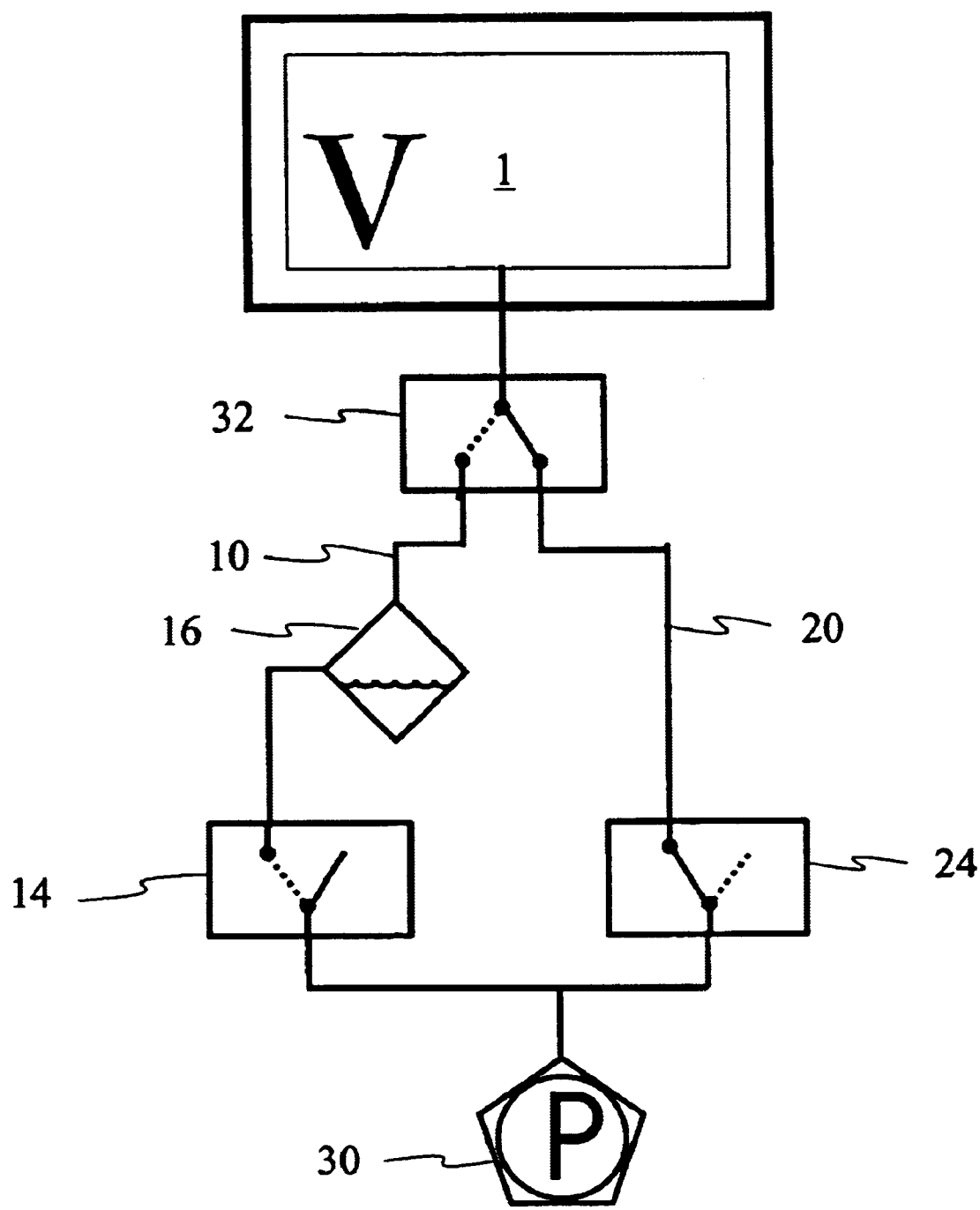
Figure 7:
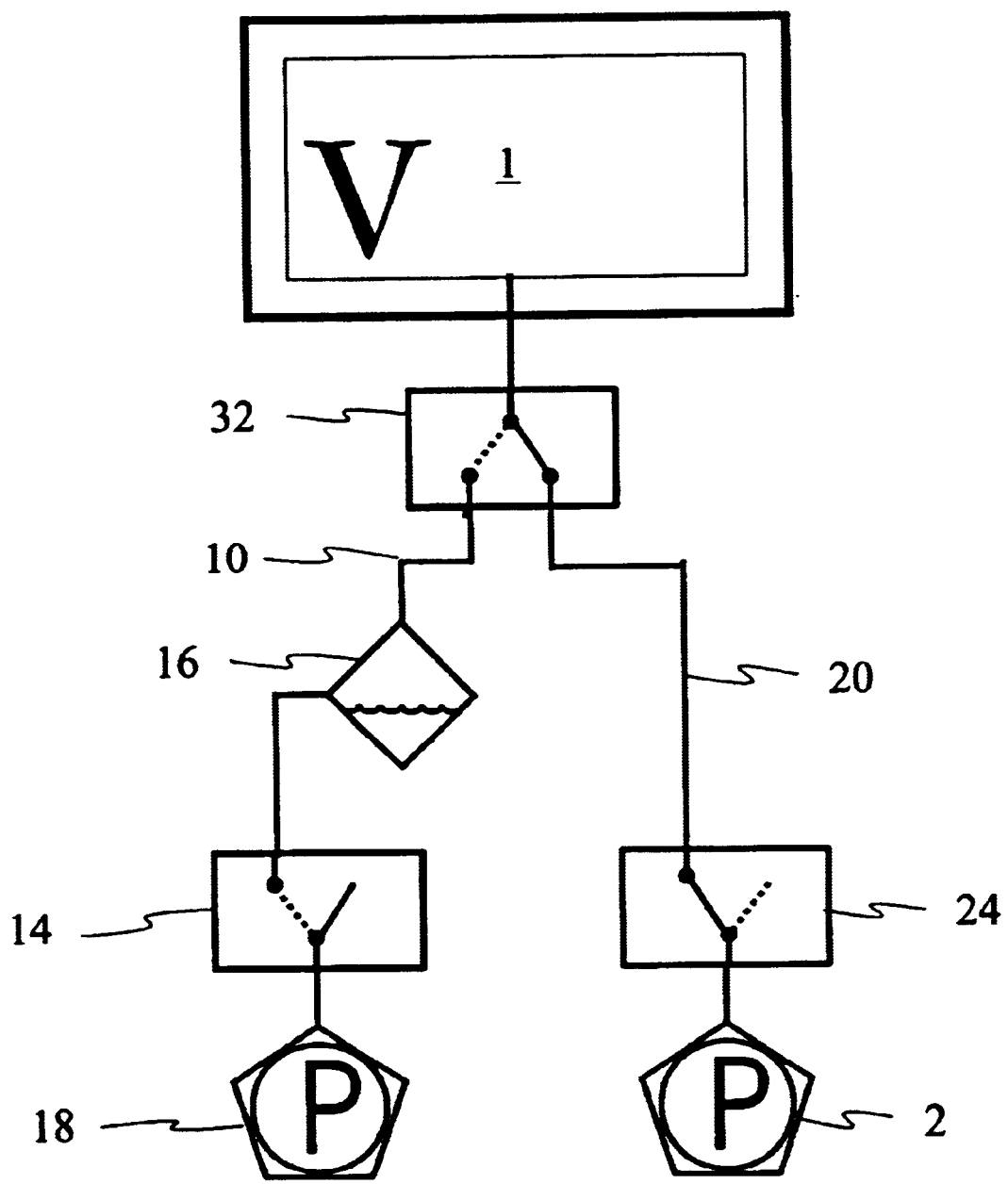

In FIG. 6 the two closure devices 12 and 22 are combined to form a joint first 3/2-way valve 32. The parts of the first and second line 10 and 20 which are arranged between the closure device and vacuum chamber are combined to form a joint upper line. The first 3/2-way valve 32 is designed so that either there is a connection from the negative pressure chamber to the first line 10 or there is a connection from the negative pressure chamber to the second line 20. The combining of the two closure devices into a 3/2-way valve simplifies the construction, as it reduces the number of lines and components in the system which have to be controlled. However, it also offers the advantage that liquid which collects in a structure as in FIG. 5 on the blocked closure device 22 and could get into the vacuum pump and damage it when the closure device was opened, cannot collect here, as it is always able to pass into the separator during the filtering process. Valves other than the 3/2-way valve may also be used at this point in the piping system. However, they must all comprise the two switching states with which the liquid and the gases to be pumped out can either enter only the separator 16 or only the pump 30. FIG. 7 differs from FIG. 6 in that one pump 30 is replaced by a vacuum pump 2 and an additional vacuum pump 18.

Figure 8:
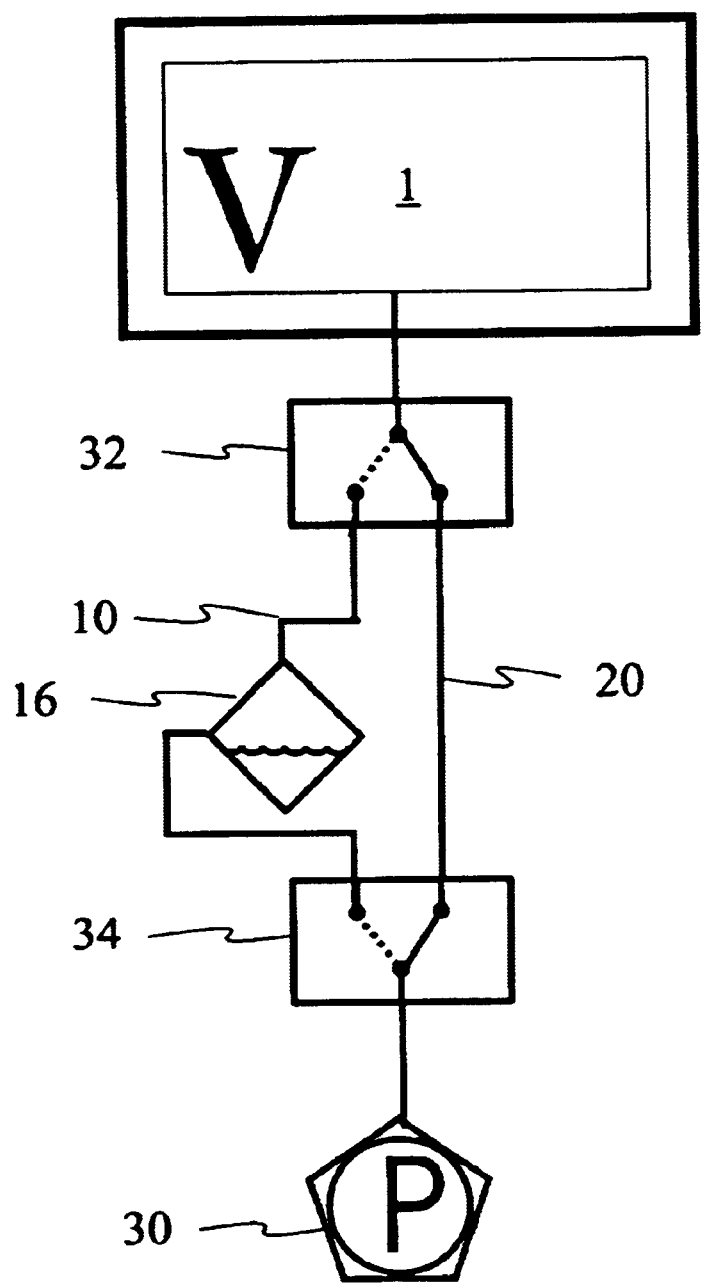

The embodiment in FIG. 8 is diagrammatically identical to that shown in FIG. 1. In this embodiment, the two closure devices 14 and 24 from FIG. 6 and FIG. 7 are also replaced by an additional 3/2-way valve 34 with the same advantages as for the embodiment in FIG. 7. In addition, it makes it possible to use only one pump. Alternatively in FIG. 7 the two pipe sections adjoining the closure devices may be combined by means of a T-shaped connector and thus passed into a single pump.

FIG. 9 shows a preferred embodiment of a negative pressure chamber 1 for treating liquids having a hotplate with holes. The drawing shows a base housing 60 with an outflow 62. Placed over the base housing is an upper housing 64, the contact surfaces between the base housing 60 and upper housing 64 essentially forming a gastight seal with one another. The lid 66 on the upper housing 64 also essentially forms a gastight seal with the upper housing 64, so that the total housing of the negative pressure chamber 1 comprising the base housing 60, upper housing 64 and lid 66 is substantially sealed in gastight manner apart from the outflow 62. In a preferred embodiment a carrier plate 78 is housed in the negative pressure chamber 1, which holds containers 70 with inlet openings 72, filter bodies 76 and outlet openings 74. In a preferred embodiment these containers are fixed to the carrier plate 78 and the carrier plate is horizontally placed on a support structure of the base housing 60. In this way a liquid can be introduced into the inlet opening 72 and sucked through the filter body when negative pressure is produced at the outflow by means of a vacuum pump. Also shown is a hotplate 80 with holes into which the containers preferably project with their outlet openings 74. Preferably, the containers may also project as far as the filter bodies or further into the holes in the hotplate. This ensures rapid drying of the liquid residues adhering in the filter bodies 76 and outlet openings 74. The hotplate with holes thus allows, for example, rapid drying after a washing operation with a washing solution such as ethanol. Moreover, a fixed temperature can be set by means of the hotplate 80, thus beneficially assisting certain chemical processes in the containers. In an advantageous embodiment, the hotplate 80 is heated by a first heating strip 84, this heating strip advantageously being passed around the hotplate. Another embodiment comprises a second heating element 86 on the wall of the negative pressure chamber, which is preferably attached to the edge of the base housing. It is advantageously a heating strip which is set into the wall. This heating element also preferably serves to dry the vacuum chamber and provides a regulatable temperature for the substances contained in the negative pressure chamber. Advantageously, heating the walls of the negative pressure chamber prevents any already evaporated ethanol from the filter from being condensed on the colder walls.

The negative pressure chamber 1 shown in FIG. 9 is also used for filtering. For this, the lid 60 is removed and the carrier plate loaded with containers is placed on the supports provided in the top part of the upper housing 64. A gasket, for example, provided at this point ensures a gastight seal. The containers hold biological samples in liquid above the filter. The operation of a vacuum pump connected to the outflow 62 creates a negative pressure inside, to allow the liquid to flow through the filter bodies 76. The liquid sucked through the filter bodies 76 is conveyed by gravity and by the suction of the vacuum pump to the outflow 62, from where it passes to the separator 16.

LIST OF REFERENCE NUMERALS 1 negative pressure chamber
2 vacuum pump
10 first line
12 first closure device
14 additional first closure device
16 separator
18 additional vacuum pump
20 second line
22 second closure device
24 additional second closure device
30 joint vacuum pump
32 first 3/2-way valve
34 additional 3/2-way valve
36 joint upper line
38 joint lower line
39 ventilation line
40 ventilation valve
42 throttle valve
44 pressure sensor
46 electronic control
48 additional separator
50 muffler
60 base housing
62 outflow
64 upper housing
66 lid
70 container
72 inlet opening
74 outlet opening
76 filter body
78 carrier plate
80 hotplate
82 holes
84 first heating strip
86 second heating strip

What is claimed is:

1. An apparatus for treating liquids in a negative pressure chamber, having a vacuum pump and a separator, the negative pressure chamber being connected to the separator by a first line and a first closure device being arranged between the negative pressure chamber and separator, while the negative pressure chamber is connected to the vacuum pump via a second line, so that the negative pressure chamber can be evacuated while avoiding the separator.

2. The apparatus according to claim 1, wherein the negative pressure chamber is connected to an additional vacuum pump via the separator.

3. The apparatus according to claim 2, wherein an additional first closure device is provided between the separator and additional vacuum pump.

4. The apparatus according to claim 1, wherein a second closure device is provided in the second line between the negative pressure chamber and vacuum pump.

5. The apparatus according to claim 3 or 4, wherein an additional second closure device is arranged in the second line.

6. The apparatus according to claim 2, wherein the vacuum pump and the additional vacuum pump are replaced by one vacuum pump.

7. The apparatus according to claim 4, wherein the first and second closure device are replaced by a first 3/2-way valve.

8. The apparatus according to claim 5, wherein the additional first and additional second closure device are replaced by an additional 3/2-way valve.

9. The apparatus according to claim 1, wherein the apparatus is an apparatus for filtering liquids.

10. The apparatus according to claim 9, wherein, when filtering liquids, the closure devices are switched to a position such that evacuation is effected with the separator.

11. The apparatus according to claim 1, wherein the apparatus is adapted for eliminating liquids in a negative pressure chamber.

12. The apparatus according to claim 11, wherein, when eliminating liquids, the closure devices are switched to a position such that evacuation is effected without the separator.

13. The apparatus according to claim 1, wherein a ventilation valve is provided on the negative pressure chamber.

14. The apparatus according to claim 13, wherein a throttle valve is provided between the ventilation valve and the negative pressure chamber.

15. The apparatus according to any one of claims 1, 2, 7, 13, or 14, wherein the apparatus comprises an electronic unit for controlling closure devices, 3/2-way valves, ventilation valve, throttle valve and/or vacuum pumps.

16. A negative pressure chamber for treating liquids, adapted for use with an apparatus according to claim 1, wherein the negative pressure chamber comprises a hotplate, with holes, for heating areas of the interior of the negative pressure chamber.

17. The negative pressure chamber according to claim 16, wherein the hotplate is heated by means of a heating strip, the heating strip being placed in the outer region of the hotplate.

18. The negative pressure chamber according to claim 16, wherein the holes in the hotplate are shaped so that containers holding liquids can project into the holes.

19. The negative pressure chamber according to claim 16, wherein the hotplate consists essentially of a heat-conducting material.

20. The negative pressure chamber according to claim 16, wherein the negative pressure chamber has at least one heating element in the region of the side wall.

21. The negative pressure chamber according to according to claim 20, wherein each heating element is a heating strip.

22. The negative pressure chamber according to according to claim 16, wherein an electronic unit regulates the hotplate.

23. A process for eliminating liquid residues in a negative pressure chamber comprising the following steps:

a) the negative pressure chamber is sealed off to be airtight;

b) the negative pressure chamber is connected to a vacuum pump and the separator is separated from the negative pressure chamber and vacuum pump;

c) the vacuum pump is switched on and the negative pressure chamber is pumped out.

24. The process according to claim 23, wherein after the pumping the negative pressure chamber is ventilated.

25. The process according to claim 24, wherein the pumping and ventilation are repeated several times.

26. The process according to claim 23, wherein the liquid residues to be eliminated contain ethanol.

27. The process according to claim 23, wherein the liquid residues are heated to accelerate the evaporation.

28. The process according to claim 27, wherein the liquid residues are heated to a temperature above their boiling point.

29. The process according to any one of claims 23 to 28, wherein the steps of the process are controlled by an electronic unit.

30. The process according to claim 29, wherein the elimination of liquids according to the process is carried out automatically by the electronic control unit.

* * * * *